United States Patent
Yantz et al.

(10) Patent No.: US 11,815,189 B2
(45) Date of Patent: Nov. 14, 2023

(54) CONFIGURABLE FLUID CHANNEL SEALING DEVICES AND METHODS

(71) Applicant: NxStage Medical, Inc., Lawrence, MA (US)

(72) Inventors: Gregory Yantz, Boxford, MA (US); Mark T. Wyeth, Andover, MA (US); James Ian Johnson, Culver City, CA (US); William J. Schnell, Libertyville, IL (US)

(73) Assignee: NxStage Medical, Inc., Lawrence, MA (US)

(*) Notice: Subject to any disclaimer, the term of this patent is extended or adjusted under 35 U.S.C. 154(b) by 266 days.

(21) Appl. No.: 17/279,023

(22) PCT Filed: Sep. 25, 2019

(86) PCT No.: PCT/US2019/052959
§ 371 (c)(1),
(2) Date: Mar. 23, 2021

(87) PCT Pub. No.: WO2020/068985
PCT Pub. Date: Apr. 2, 2020

(65) Prior Publication Data
US 2022/0074511 A1 Mar. 10, 2022

Related U.S. Application Data

(60) Provisional application No. 62/736,729, filed on Sep. 26, 2018.

(51) Int. Cl.
*F16K 17/40* (2006.01)
*A61M 1/16* (2006.01)
(Continued)

(52) U.S. Cl.
CPC ............. *F16K 13/04* (2013.01); *A61J 1/10* (2013.01); *A61J 1/2027* (2015.05);
(Continued)

(58) Field of Classification Search
CPC ........ F16K 13/04; A61M 1/1668; A61M 1/28; A61M 2209/04; A61M 39/221; A61J 1/10; A61J 1/2027
(Continued)

(56) References Cited

U.S. PATENT DOCUMENTS 3,913,207 A * 10/1975 Frey .................. B23P 17/00
65/DIG. 9
3,977,409 A * 8/1976 Brendling ............. A61M 39/22
251/342
(Continued)

FOREIGN PATENT DOCUMENTS

EP 0555927 A1 8/1993
NZ 605451 A 8/2014

OTHER PUBLICATIONS

Extended European Search Report dated May 31, 2022 for European Patent Application No. 19867185.1.
(Continued)

*Primary Examiner* — Minh Q Le
(74) *Attorney, Agent, or Firm* — Potomac Law Group, PLLC

(57) ABSTRACT

Fluid channel sealing devices, frangible seals, fluid circuits, associated controllers and methods of using the same are provided for controlling fluid distribution using a reconfigurable blocking element having first and second portions to establish a first configuration free of any open channels such that fluid is prevented from flowing through the channel and
(Continued)

a second configuration where the first and second portions are separated to establish an open channel and allow fluid to pass.

15 Claims, 5 Drawing Sheets

(51) Int. Cl.
    *A61M 1/28*     (2006.01)
    *A61M 39/22*     (2006.01)
    *A61J 1/10*     (2006.01)
    *A61J 1/20*     (2006.01)

(52) U.S. Cl.
    CPC ............ *A61M 1/1668* (2014.02); *A61M 1/28* (2013.01); *A61M 39/221* (2013.01); *A61M 2209/04* (2013.01)

(58) Field of Classification Search
    USPC ......... 137/68.11; 251/75, 342; 604/403, 415
    See application file for complete search history.

(56) References Cited

U.S. PATENT DOCUMENTS

| | | | |
|---|---|---|---|
| 4,181,140 A * | 1/1980 | Bayham | A61J 1/00 137/68.28 |
| 4,294,247 A * | 10/1981 | Carter | A61M 39/221 604/905 |
| 4,340,049 A | 7/1982 | Munsch | |
| 4,396,382 A | 8/1983 | Goldhaber | |
| 4,439,188 A | 3/1984 | Dennehey et al. | |
| 4,462,430 A | 7/1984 | Anthony et al. | |
| 4,586,928 A | 5/1986 | Barnes et al. | |
| 5,330,464 A | 7/1994 | Mathias et al. | |
| 5,826,621 A * | 10/1998 | Jemmott | A61M 39/281 137/853 |
| 6,132,413 A * | 10/2000 | Mathias | A61M 39/221 604/408 |
| 6,322,551 B1 | 11/2001 | Brugger | |
| 7,507,226 B2 | 3/2009 | Stanus et al. | |
| 8,152,116 B2 | 4/2012 | Westberg | |
| 8,172,823 B2 | 5/2012 | Rondeau et al. | |
| 8,469,931 B2 | 6/2013 | Tryggvason et al. | |
| 9,192,756 B2 * | 11/2015 | Deverre | A61M 39/221 |
| 10,166,382 B2 * | 1/2019 | Sala | A61M 39/221 |
| 10,765,855 B2 * | 9/2020 | Brückner | A61M 39/281 |
| 2006/0135951 A1 | 6/2006 | Meek et al. | |
| 2010/0132512 A1 | 6/2010 | Bucciaglia et al. | |
| 2012/0269934 A1 | 10/2012 | Ramsey et al. | |
| 2014/0263529 A1 | 9/2014 | Stonig | |
| 2014/0306447 A1 | 10/2014 | Werth | |
| 2015/0093450 A1 | 4/2015 | Riser et al. | |

OTHER PUBLICATIONS

International Search Report and Written Opinion dated Feb. 4, 2020 for International Patent Application No. PCT/US2019/052959.
Invitation to Pay Additional Fees dated Nov. 22, 2019 for International Patent Application No. PCT/US2019/052959.

* cited by examiner

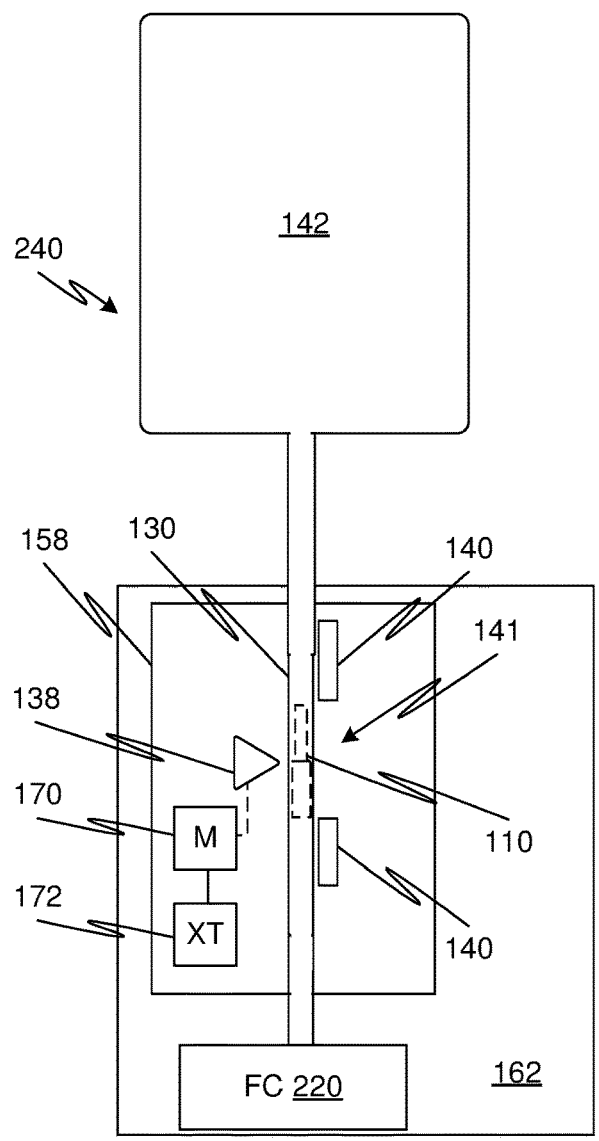
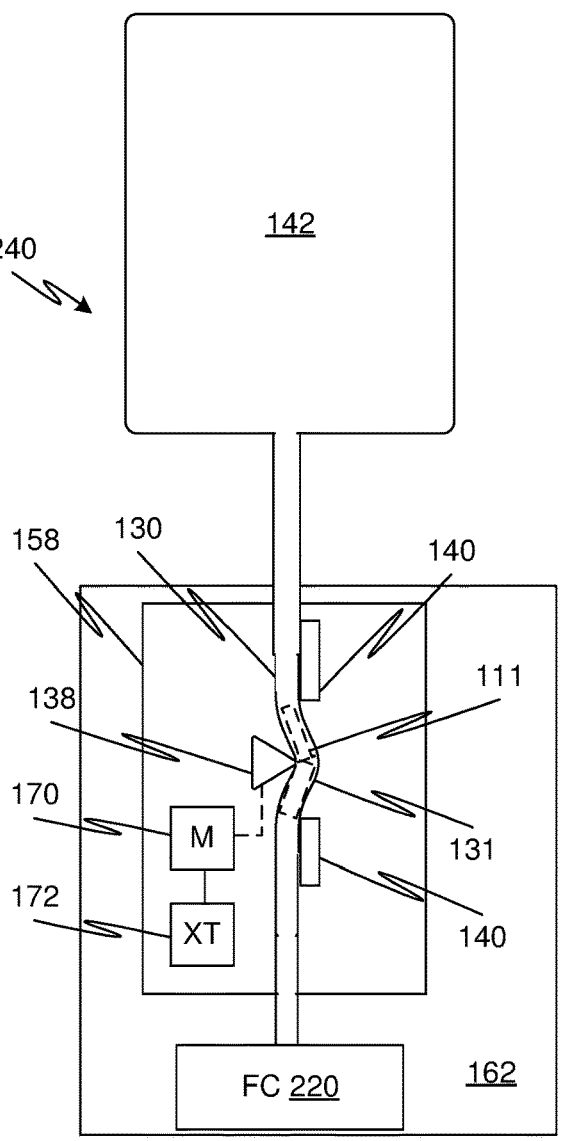
Fig. 4A  Fig. 4B
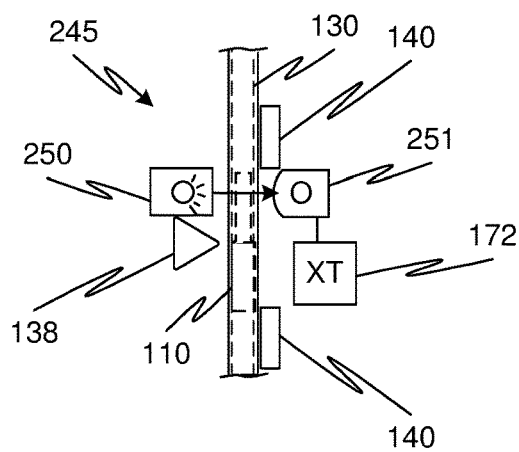
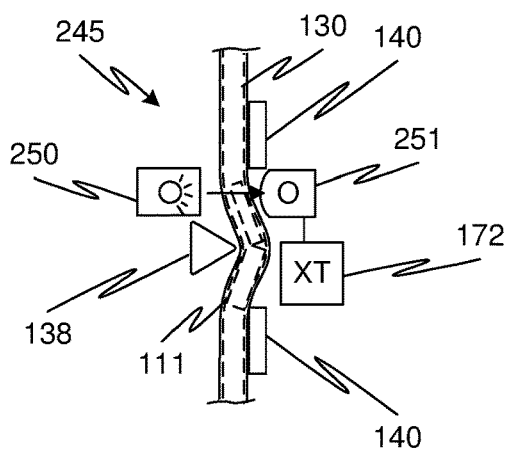
Fig. 4C  Fig. 4D

CONFIGURABLE FLUID CHANNEL SEALING DEVICES AND METHODS

CROSS-REFERENCE TO RELATED APPLICATIONS

This Application is a U.S. national stage filing under 35 U.S.C. § 371 of International Application No. PCT/US2019/052959, filed Sep. 25, 2019, which claims priority to and the benefit of U.S. Provisional Patent Application No. 62/736,729 filed Sep. 26, 2018, each of which are incorporated herein by reference in their entireties.

BACKGROUND

For numerous reasons plastic tubes or tubes made of other materials are frequently used to deliver medications and fluids to patients in hospital and outpatient settings. A known device for sealing tubes, or kinds of channels, to isolate containers of fluid from connectors or other portions of a fluid circuit from the fluid is a frangible seal. Frangible seals of a known type include a breakable plug that seal a tube when intact and once broken allow a fluid to flow. One type of frangible seal is an elongate member frictionally engaged with and sealed to the inside of a tube. The elongate member is gripped from opposite ends and bent until it breaks. The breakage creates a defined opening that allows fluid to flow. The defined opening is formed by a weakened area. Once broken, the tube may relax which may cause the broken pieces of the elongate member partially, if not completely, fail to ensure the patency of the tube. In prior art devices, this may be overcome by an elongate member whose parts may separate after fracture and displaced apart by working the tube back and forth a few times to "crawl" one part away from the other or both parts away from each other.

SUMMARY

Objects and advantages of embodiments of the disclosed subject matter will become apparent from the following description when considered in conjunction with the accompanying drawings.

Aspects described herein provide a sealing device for a tube, or more generally, a fluid channel. The fluid channel has internal walls to provide for the conveyance of a fluid and a blocking element that is sealingly engaged with the internal walls. The blocking element can be formed such that it is reconfigurable from a first configuration, where it is free of any open channels such that fluid is prevented from flowing through the channel, and a second configuration in which an open channel is established allowing fluid to pass.

Further aspects provide a frangible seal having a blocking element (e.g., a solid of rotation about an axis of the blocking element). The blocking element may be fitted in a tube to block the flow of fluid in the tube, for example to isolate a container of fluid from a component or components connected by the tube to the container. In one aspect, the container fluid is sterile (e.g., sterilized saline or other biomedical or medical treatment fluids).

In this aspect, the blocking element has a first and a second part connected in the middle. The first part of the blocking element has a diameter smaller than the second part of the blocking element, and the second part defines a hollow cylinder with a first end being open and a second opposite end being closed by an end of the first part. In another aspect, the second part is a tapered hollow cylinder (e.g., a cylinder with a top portion diameter that is larger the bottom portion diameter). In yet another aspect, the diameter of the first part has a minimum dimension that is smaller than a diameter of the second part. In this aspect, the term "minimum dimension" refers to the smallest diameter that permits the first part of the blocking element to perform at least one of its functions (e.g., prevent fluid flow).

This aspect may also have a characteristic shape and material selection such that when the blocking element is reconfigured to allow a flow of fluid, the blocking element remains a single piece rather than separate pieces being created. In embodiments, a web of material connects the first and second parts and remains intact to hold the first and parts together such that when a force is applied crosswise to said axis (or an elongate dimension of the blocking element), the first and second only partly separate to open said hollow cylinder second end. After the first and second parts partly separate, the fluid can flow through the hollow cylinder first end, out the hollow cylinder second end, and around the first part, which is smaller in diameter, to permit a free flow of fluid. In this aspect, the first part, which may be too small to engage with the tube reliably, is prevented from carried away by the flow of fluid and through the tube after the blocking element is reconfigured. In embodiments, the blocking element is reconfigured by bending the outside of the tube. A tube of resilient plastic, commonly used in medical applications, would tend to return to its original shape thereby potentially causing the first and second parts to return to a blocking or partly blocking configuration. Thus, in embodiments, the bent configuration of the tube is maintained by an automated device that both reconfigures the blocking element and maintains it in its reconfigured state selected to provide a selected degree of patency in the tube.

Another aspect of the disclosed embodiments is that the blocking element may be formed such that it has a shape that allows the part to be injection molded from hard polymer and released readily from the mold. That is, the shape may include only positive or neutral draft angles to permit release. Further the blocking element shape may be such that it can be formed in a two-part mold.

Further objects and advantages of the aspects described herein will be evident from the following disclosure.

BRIEF DESCRIPTION OF THE DRAWINGS

Aspects will hereinafter be described in detail below with reference to the accompanying drawings, wherein like reference numerals represent like elements. The accompanying drawings have not necessarily been drawn to scale. Where applicable, some features may not be illustrated to assist in the description of underlying features.

FIG. 4A shows an exemplary plastic tubing containing a fluid channel in a first configuration connected to connected to a fluid container, according to embodiments of the disclosed subject matter.

FIG. 4B shows the exemplary plastic tubing of FIG. 4A in a second configuration permitting flow from a container, according to embodiments of the disclosed subject matter.

FIGS. 4C and 4D show an installation verification component that may be employed with systems and devices shown in FIG. 4B or similar systems and devices, according to embodiments of the disclosed subject matter.

DETAILED DESCRIPTION

Figure 1A:
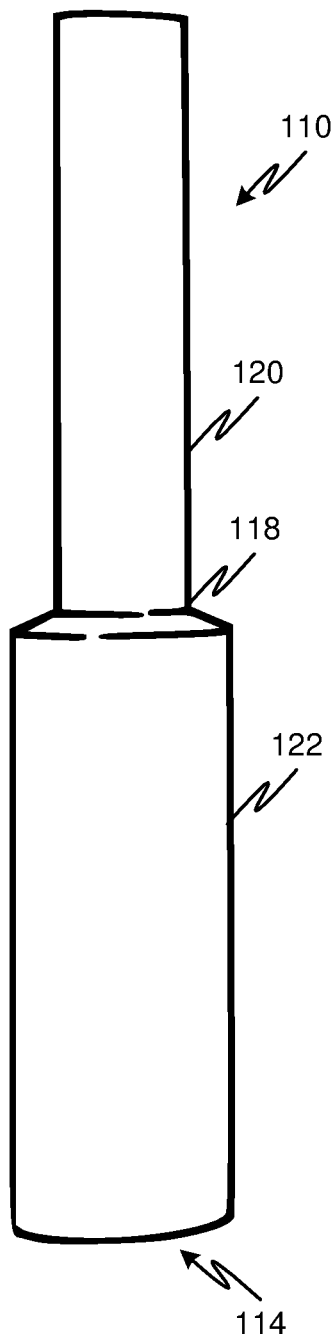
FIG. 1A shows an outer view of an exemplary fluid channel blocking element.

Features of the disclosed aspects may be combined, rearranged, omitted, etc., within the scope of the description herein to produce additional aspects. Furthermore, certain features may sometimes be used to advantage without a corresponding use of other features. The numbered elements refer to examples of features depicted in the drawings and other configurations of the depicted aspects may be used.

Aspects described herein provide a fluid channel sealing device having internal walls to provide for the conveyance of a fluid. The fluid channel sealing device can have a blocking element sealingly engaged with the internal walls. In this aspect, the blocking element can be reconfigured from a first configuration where it is free of any open channels such that fluid is prevented from flowing through the channel, and a second configuration in which an open channel is established allowing fluid to pass.

The second configuration can be established by deforming the blocking element to open a hole in the blocking element. The hole may be kept open despite the tubing tending to relax and revert to its straightened by maintaining the second deformed shape. The openness of the hole can be being maximized by maintaining or continuously maintaining a deformed configuration of the blocking element or by applying a deforming force to the blocking element. Note that in the deformed configuration, the blocking element is fractured by the deforming force.

In one aspect, the blocking element is a solid of rotation, for example, a solid of rotation with an axis aligned with an axis of the fluid channel. In another aspect, the blocking element is reconfigurable by applying a force crosswise to the axis of the blocking element. The term "solid of rotation," as used herein, refers to a solid figure obtained by rotating a plane curve around an axis of revolution that lies on the same plane. The blocking element may be of any suitable material for example, but not limited to, e.g., polystyrene, polyvinylchloride, polyolefins, polydimethylsiloxane, polystyrene, and nylon.

In yet another aspect, the blocking element is a frangible solid and the second configuration is established by fracturing it. In a further aspect, the second configuration is established by fracturing the blocking element to form a hole, where the patency of the hole is maximized by preventing the blocking element, once in its fractured state, from returning to the first configuration thereby preventing the hole from being closed or partially blocked due to the tendency of an enclosing plastic tube to relax and return the blocking element back to the first configuration. In this aspect, the patency of the hole is maintained by preventing a blocked tube from causing the blocking element partially returning to the first configuration to close or partially occlude the hole.

As used herein, the term "frangible" refers to a solid or portion of a solid that can be deformed or detached in whole or part from another component or itself. For example, in one aspect, the blocking element can be readily removed or detached from the fluid channel sealing device with a selected force applied when moving the fluid channel sealing device from the first configuration to the second configuration. In another aspect, the force required to fracture the frangible solid should more than required to permit the fluid channel device to perform its function in the first configuration without fracturing the blocking element. Such functions may include manual installation of a fluid circuit containing the blocking element into a device that pumps fluid through the tube, rough handling that may occasion such manual installation, shipping and storage of the tube and attached components, and other functions.

Optionally, a forcing driver can be attached to a holder for the fluid channel (e.g., tube). The holder can be aligned with the channel such that the blocking element is aligned with the forcing driver. The term "aligned with the forcing driver" specifies that the forcing driver is located in a position where it can change the blocking element from the first configuration to the second configuration. In embodiments, the forcing driver is a member that is displaced crosswise against the tube holding the blocking element to generate a force crosswise to the axis of the blocking element. The forcing driver may be driven from a closed state to an open state in which it holds the blocking element after fracturing to maintain patency of the hole. The transition of the forcing element from the closed state to the open state (closed and open referring to the patency of the tube blocked by the blocking element) being effective to cause the reconfiguration of the blocking element, for example, its fracture.

Note the forcing driver can take a variety of different forms. It may include a linear actuator, a spring, a solenoid and may be automatic or manually operated.

The blocking element may be incorporated in a fluid circuit with a filled container connected to other parts of the fluid circuit. For example, the fluid circuit could be a blood circuit, for extracorporeal blood processing, with a pre-attached bag of priming fluid connected by a tube blocked by the blocking element. The fluid circuit with the blocking element may be configured for attachment to a predefined fluid management apparatus that includes an automated forcing driver under control of a motor and a controller. The fluid circuit may be loaded into the fluid management device in a predefined way such that the forcing driver is able to act on the blocking element in the manner described and under control of the controller.

Note that although the embodiments disclosed include blocking element that have a form of a solid of rotation, it should be evident from the disclosure that other embodiments are possible. For example, the first part outside and the second part inside may have a non-round shape and still form a seal with a round tube. Such a variant would even permit release from a two-part mold.

Further aspects provide a frangible seal having a blocking element that has first and second parts connected in a middle by a circumnavigating thin web of material (e.g., polystyrene, polyvinylchloride, polyolefins, polydimethylsiloxane, polystyrene, nylon) that tears or fractures reliably when a predefined force is applied crosswise to an elongate dimension or axis thereof. In embodiments, the first part of the blocking element (e.g., a uniform-diameter solid cylinder, although it is clear it may be tapered or have other shapes) has a dimension transverse to the long dimension of the blocking element that is smaller than the second part. In a cylindrical embodiment, the first part transverse dimension may be its diameter. The second part may define a hollow structure (e.g., a hollow cylinder) with an open first end a second opposite end closed by an end of the first part. The first and second parts may be connected by the web of material.

In another aspect, a minimum size opening of the hole is maintained by preventing the blocking element from returning to an "initial configuration" which can be defined as a configuration wherein the web is intact.

The web connecting the first and second parts can be sufficiently thin such that when a force is applied crosswise to the axis, the first and second parts at least partly separate to open the second end of the hollow cylinder such that fluid can flow into the first end of the hollow cylinder, out the second end of the hollow cylinder, and around the first part when the frangible seal is fitted in a flow channel with an internal diameter that forms a seal with the second part. The smaller size of the first part may facilitate flow around it. The magnitude of the bent condition of the tube holding the blocking element may be optimized for patency. That is, for the configuration of the blocking element, there may be an optimal magnitude of the bent condition of the tube that minimizes the flow resistance.

In embodiments, the blocking element is a shape other than a solid of rotation but is formed such that it can be reconfigured by a forcing driver pressed against it from any approach angle that is generally transverse to its longitudinal dimension (or axis of its maximum dimension).

In another aspect, the frangible seal includes a flexible tube fitted with the blocking element. In yet another aspect, the flexible tube is connected to a fluid-filled container that is sealed by the blocking element. In another aspect, the blocking element is of a material that permits sufficient bending that a portion of the web remains intact after reconfiguration thereby ensuring the first and second parts are not separated as a result of flowing fluid after the first and second parts partly separate by the reconfiguring thereof.

The frangible seal can also include a flexible tube fitted with the blocking element and an opening device configured with a forcing driver that applies a force against an outside of the flexible tube, crosswise to said axis. This force can maintain the pusher against the flexible tube to prevent the first and second parts from being urged back toward a collinear configuration in which the first part covers the hollow cylinder second end, thereby maintaining patency of the hollow cylinder second end.

Further aspects provide methods of sealing a channel with a fluid channel sealing device by sealingly engaging a blocking element with the internal walls of a fluid channel for the conveyance of a fluid. In this aspect, the blocking element is reconfigurable from a first configuration where it is free of any open channels such that fluid is prevented from flowing through the channel to a second configuration in which an open channel is established allowing fluid to pass.

In another aspect, the second configuration is established by deforming the blocking element to open a hole in the blocking element in which the patency of the hole is maximized by maintaining a deformed configuration of the blocking element. In a further aspect, the second configuration is established by deforming the blocking element to open a hole in the blocking element where the patency of the hole is maintained by continuously maintaining a deformed configuration of the blocking element.

In yet another aspect, the second configuration is established by deforming the blocking element to open a hole in the blocking element where the patency of the hole is maintained by continuously applying a deforming force to the blocking element. In yet another aspect, the blocking element is a solid of rotation (e.g., a solid of rotation with an axis aligned with an axis of the fluid channel).

The blocking element can be reconfigured (e.g., from a first to a second configuration) by applying a force crosswise to the axis of the blocking element. The second configuration can also be established by deforming the blocking element to open a hole in the blocking element, where the patency of the hole is maximized by maintaining or continuously maintaining a deformed configuration of the blocking element, or by continuously applying a deforming force to the blocking element.

In another aspect, the blocking element is a frangible solid and the second configuration is established by fracturing it. In yet another aspect, the second configuration is established by breaking the frangible solid to establish a hole and maximizing the patency of the hole by preventing the blocking element in its fractured state from returning to the first configuration.

In a further aspect, the second configuration is established by fracturing the blocking element to open a hole in the blocking element and patency of the hole is maintained by preventing a first part of the blocking element from closing a hole in a second part or at least minimizing or reducing the occlusion of the hole by the first part.

Further aspects include use of forcing driver attached to a holder for the fluid channel. In this aspect, the holder aligns the channel such that the blocking element is aligned with the forcing driver. In this aspect, the blocking element is a solid of rotation (e.g., a solid of rotation with an axis aligned with an axis of the fluid channel). In yet another aspect, the method of claim force driver generates a force crosswise to the axis of the blocking element. In another aspect, the forcing driver holds or retains the blocking element after fracturing to maintain patency of the hole.

Figure 1B:
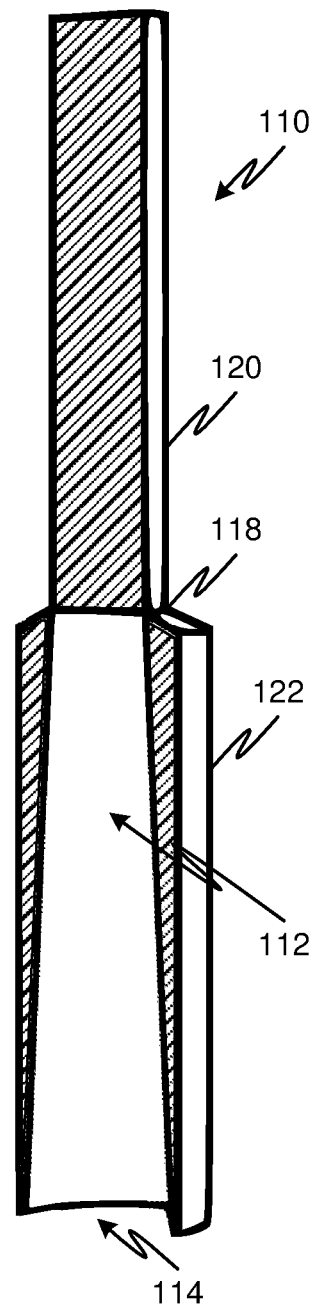
FIG. 1B is a section of the exemplary fluid channel blocking element.

With reference to FIG. 1A, a blocking element 110 has a first part 120, a second part 122 with a channel opening 114 formed therein connected by a web portion 118. FIG. 1B shows a longitudinal section of blocking element 110 revealing a channel 112 to which the channel opening 114 opens. From FIGS. 1A and 1B it may be observed that the blocking element 110 features positive and/or neutral draft angles and is configured with no overhangs as viewed from the top and bottom such that it can be molded and separated from a rigid two-part mold. The blocking element 110 is also formed such that the second part 122 is round and can form a seal with the wall of a tube when inserted therein. A suitable tube, to be sealed by the blocking element 110 may be of flexible polymer such as PVC and of a diameter that is slightly less than a diameter of the second part 122 such that it may frictionally engage the internal wall of the tube and form a seal between the tube and the blocking element 110 such that flow through the tube is blocked. The blocking element may also be attached to a tube by adhesive bonding or by ultrasonic welding for example.

Figure 2A:
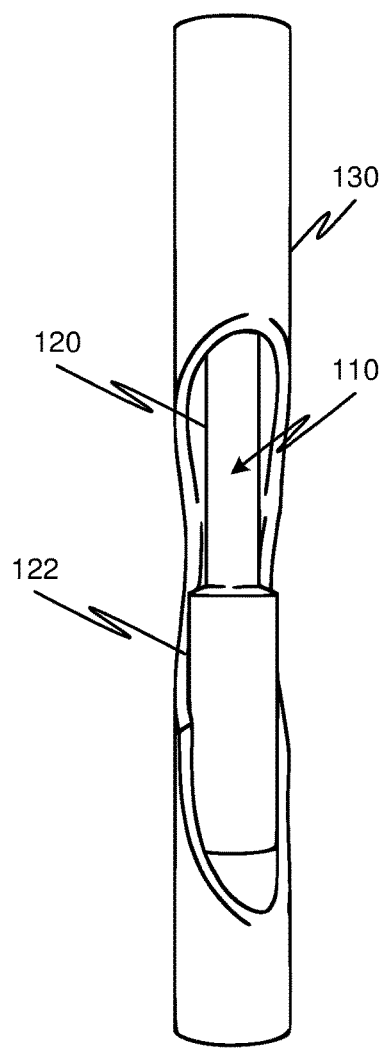
FIG. 2A shows a cutaway view of a blocking element disposed in plastic tubing and in a first sealed configuration, according to embodiments of the disclosed subject matter.

FIG. 2A shows the blocking element 110 inserted in a tube 130 such that it is frictionally engaged therewith. The tube 130 is partly cut away in this view. It will be observed that the blocking element 110 fully occludes, blocks, and prevents flow, through the tube 130 in this configuration.

Figure 2B:
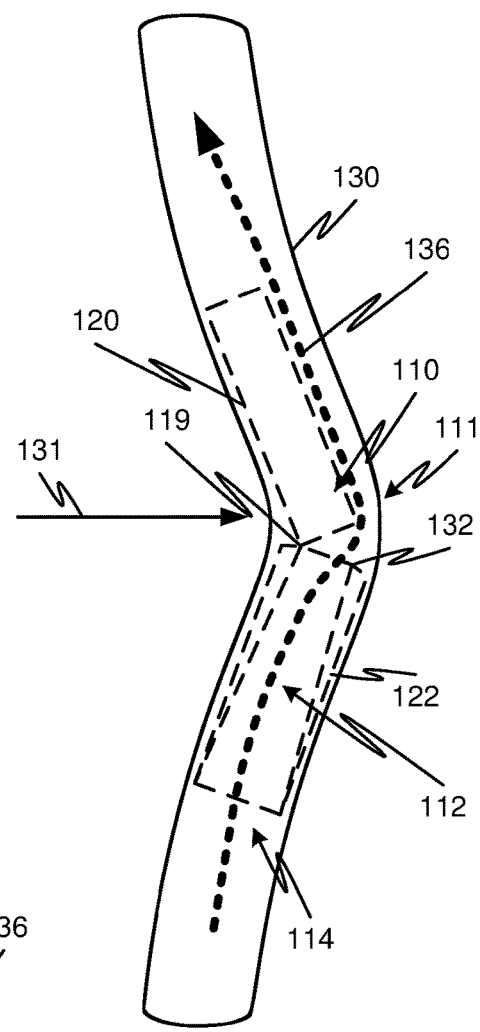
FIG. 2B shows the exemplary blocking element in a second configuration within the plastic tubing in which it is no longer sealing the tube, according to embodiments of the disclosed subject matter.
Figure 3:
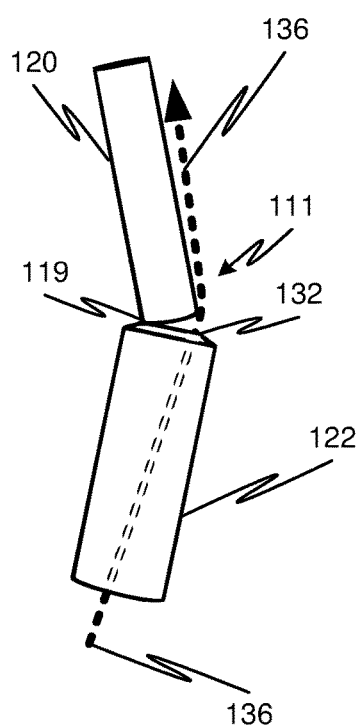
FIG. 3 shows the blocking element in the second configuration without the plastic tubing, according to embodiments of the disclosed subject matter.

FIG. 2B shows an exemplary cross section view of blocking element 110 inside tubing 130 in second configuration caused by bending the tube 130 at a location indicated an arrow 131 such that an open channel 132 is established allowing fluid to pass as indicated by the arrow 136. Fluid thus may flow through the opening 114, through the channel 112, through the opening 132, along the blocking element first part 120 and beyond the blocking element 110. Fracturing of the web 118 results in a tethering web portion 119 that remains to hold the blocking element first part 110 connected to the blocking element second part 122. A remainder of the web 118 is torn or broken. FIG. 3 shows the blocking element in the second configuration of FIG. 2B without the tube 130 and without the features shown as hidden lines in FIG. 2B such as the channel 112. That is, FIG. 3 shows the blocking element in the second configuration from the outside as it would look after reconfiguration apart from the tube. This view is for illustrative purposes and would not arise ordinarily in use.

FIG. 4A shows an example of a system that employs the blocking element 110. A fluid container such as a medical fluid bag 142 is attached by a tube 130 to a fluid circuit 220. The tube 130 is blocked in FIG. 4A by the blocking element 110 shown in broken lines. A breaking device 158 has a holder 140 that acts as a backstop but provides a gap 141 (alternatively the gap 141 may be replaced with a recess) to permit a forcing driver 138 to be forced against the tube 130 to reconfigure (e.g., fracture) the blocking element 110 within the tube 130 as indicated in FIG. 4B with the reconfigured blocking element indicated at 111. The forcing driver 138 may be driven by a motor 170 under control of a controller 172, for example a programmable controller. The holder 140 may align the tube such that the blocking element 110 is aligned with the forcing driver 138. In the configuration of FIG. 4A, the contents of the container 142 are isolated from the fluid circuit 220. Thus, the container 142 is effectively closed. In the configuration of FIG. 4A, the forcing driver 138 is in a retracted position to permit blocking element 110 to retain its first configuration which is free of any open channels such that fluid is prevented from flowing through the channel.

In FIG. 4B the blocking element 110 is shown being maintained in the second configuration where the tube 130 is bent as indicated at 131 and in which an open channel is established and maintained, allowing fluid to pass. In the configuration of FIG. 4B, fluid in the container is available to the fluid circuit 220. The fluid circuit 220 may contain a pump, for example, and a treatment device, such as a dialyzer or a blood circuit. Fluid may thus be pumped by the fluid circuit 220 to perform some operation that consumes or uses the fluid in the fluid container 142. Note that the fluid circuit 220 may be integrally attached to the tube 130 and the container 142 so as to form a sealed unit. This provides the benefit of a device that can be sterilized as a unit, for example, by autoclaving or gamma sterilization after it is fully integrated and sealed from the environment. The use of the blocking element to establish flow communication between the fluid circuit 220 and the container 142 can be performed without making any manual or automatic fluid channel connections that might otherwise introduce a risk of contamination. In embodiments, the breaking device 158 may be a part of an actuator device that engages with, and performs a function in interoperation with, fluid circuit 220. For example, a renal replacement therapy machine such as a peritoneal dialysis cycler or extracorporeal blood treatment device may have actuators and sensors that engage with the fluid circuit 220 and receive an encompassing fluid circuit 240 that includes the container 142, and the tube 130 with the blocking element 110 as well as the fluid circuit 220. The breaking device 158 and the controller 172 may thus form part of an encompassing device that receives and engages the encompassing fluid circuit 240 and interoperates with it. And the controller 172 may be one that forms a part of such an encompassing device. Again, the latter may be a medical treatment device, a fluid preparation device, or other type of machine.

FIGS. 4C and 4D show an installation verification component 245 that may be employed, for example, as part of the breaking device 158 or as part of an encompassing device with systems and devices shown in FIG. 4B or similar systems and devices. The verification component 245 in the present embodiment uses a sensor 250, 251 which may include, for example, an optical source 250 that directs light at the tube 130 an optical detector 251 that receives light from the optical source 250. The controller 172 is configured to store a range of magnitudes of the light received by it that correspond to a correct alignment of the tube 130 and the blocking element 110. If the blocking element is incorrectly positioned in the tube 130 or it is missing then the magnitude of the light received by the optical detector 251 will fall below the range. The controller 172 may then generate an error signal including, for example, an instruction to a user output on a display to replace or adjust the fluid circuit containing the tube 130.

Figure 5:
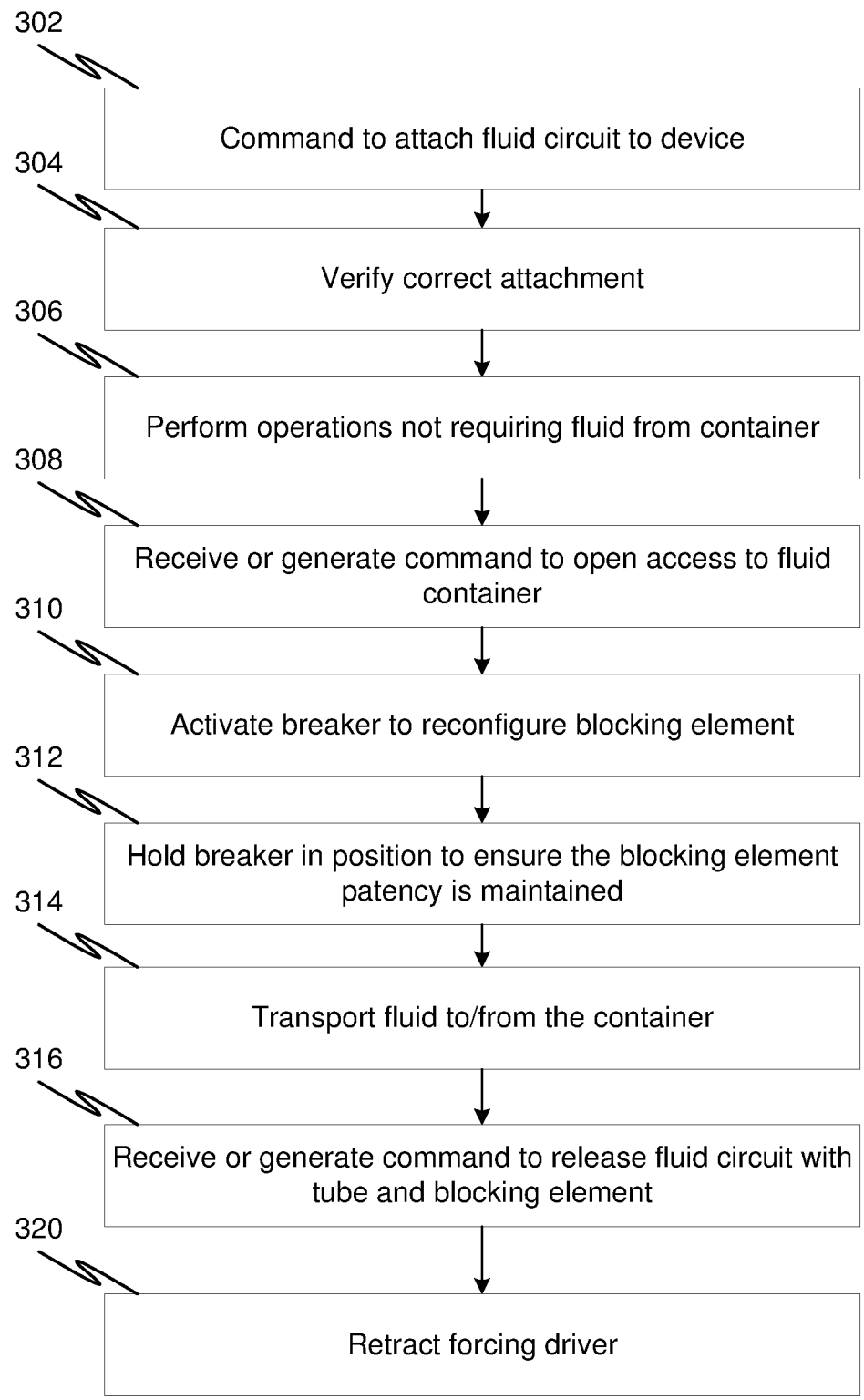
FIG. 5 shows a method of using the sealing device disclosed in an example system according to embodiments of the disclosed subject matter, according to embodiments of the disclosed subject matter.

In a method embodiment, a controller performs the method of FIG. 5. At 302 a command may be generated by the controller or received by the controller to attach a fluid circuit including the blocking element. The controller may, at 304 verify the correct attachment using, for example, the apparatus of FIGS. 4C and 4D. If incorrect attachment is detected or the breaking element is not positioned correctly or missing, an error signal may be generated. At 306, the encompassing device may perform various functions such as verification of sensors and correct attachment of consumable components and/or a patient. Then at 308 a command may be generated or received to reconfigure the blocking element to open the fluid container to a remainder of a fluid circuit. At 310, the blocking element is reconfigured to provide patency in the tube. At 312, the forcing element may continue to apply a force to the tube to hold the tube in a patent configuration by holding the tube back from restoring itself toward a straightened configuration which may allow the blocking device to occlude flow. Then at 314, the device that consumes or otherwise uses the fluid then uses the fluid which may include pumping it from the container. At 316, a command may be received or generated indicating that the fluid from the container, or its attachment through the tube for other purposes, is no longer required and at 320, the forcing driver may be retracted. At this point, a pinch clamp (not shown) may close the tube automatically to prevent any further flow from the container.

The fluid channel sealing device as described herein can be used for any application related to flow control of liquids including, but not limited, medical fluids, water, lubrication, cooling and heating systems, etc. Aspects described herein can be adapted to permit ease of control of any fluid distribution system.

Figure 6:
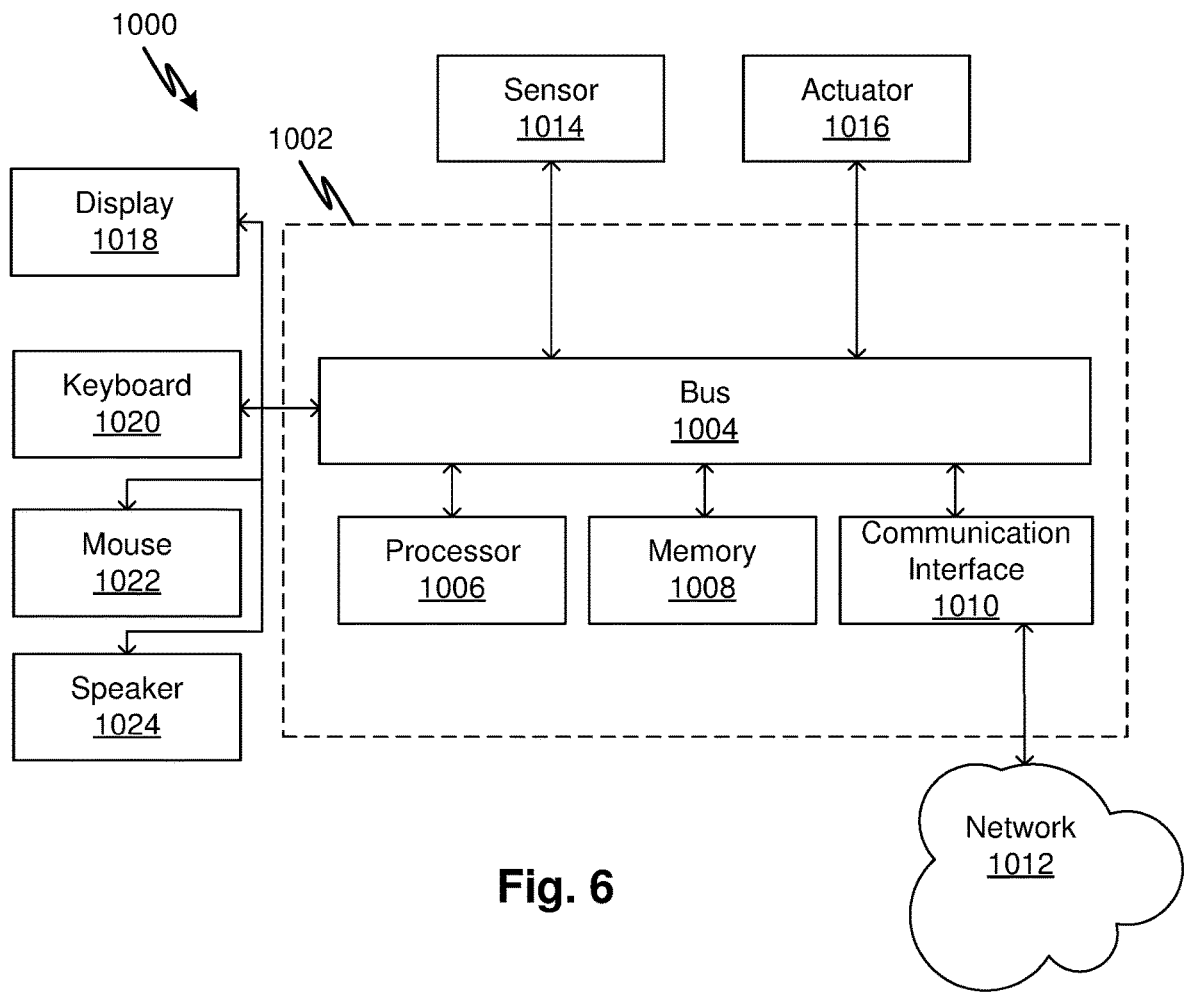
FIG. 6 shows a block diagram of an example computer system that may represent details of a controller according to various embodiments of the disclosed subject matter.

FIG. 6 shows a block diagram of an example computer system according to embodiments of the disclosed subject matter. In various embodiments, all or parts of system 1000 may be included in a medical treatment device/system such as a renal replacement therapy system. In these embodiments, all or parts of system 1000 may provide the functionality of a controller of the medical treatment device/systems. In some embodiments, all or parts of system 1000 may be implemented as a distributed system, for example, as a cloud-based system.

System 1000 includes a computer 1002 such as a personal computer or workstation or other such computing system that includes a processor 1006. However, alternative embodiments may implement more than one processor and/or one or more microprocessors, microcontroller devices, or control logic including integrated circuits such as ASIC.

Computer 1002 further includes a bus 1004 that provides communication functionality among various modules of computer 1002. For example, bus 1004 may allow for communicating information/data between processor 1006 and a memory 1008 of computer 1002 so that processor 1006 may retrieve stored data from memory 1008 and/or execute instructions stored on memory 1008. In one embodiment, such instructions may be compiled from source code/objects provided in accordance with a programming language such as Java, C++, C#, .net, Visual Basic™ language, LabVIEW, or another structured or object-oriented programming language. In one embodiment, the instructions include software modules that, when executed by processor 1006, provide renal replacement therapy functionality according to any of the embodiments disclosed herein.

Memory 1008 may include any volatile or non-volatile computer-readable memory that can be read by computer 1002. For example, memory 1008 may include a non-transitory computer-readable medium such as ROM, PROM, EEPROM, RAM, flash memory, disk drive, etc. Memory 1008 may be a removable or non-removable medium.

Bus 1004 may further allow for communication between computer 1002 and a display 1018, a keyboard 1020, a mouse 1022, and a speaker 1024, each providing respective functionality in accordance with various embodiments disclosed herein, for example, for configuring a treatment for a patient and monitoring a patient during a treatment.

Computer 1002 may also implement a communication interface 1010 to communicate with a network 1012 to provide any functionality disclosed herein, for example, for alerting a healthcare professional and/or receiving instructions from a healthcare professional, reporting patient/device conditions in a distributed system for training a machine learning algorithm, logging data to a remote repository, etc. Communication interface 1010 may be any such interface known in the art to provide wireless and/or wired communication, such as a network card or a modem.

Bus 1004 may further allow for communication with a sensor 1014 and/or an actuator 1016, each providing respective functionality in accordance with various embodiments disclosed herein, for example, for measuring signals indicative of a patient/device condition and for controlling the operation of the device accordingly. For example, sensor 1014 may provide a signal indicative of a viscosity of a fluid in a fluid circuit in a renal replacement therapy device, and actuator 1016 may operate a pump that controls the flow of the fluid responsively to the signals of sensor 1014.

Figures 7A, 7B:
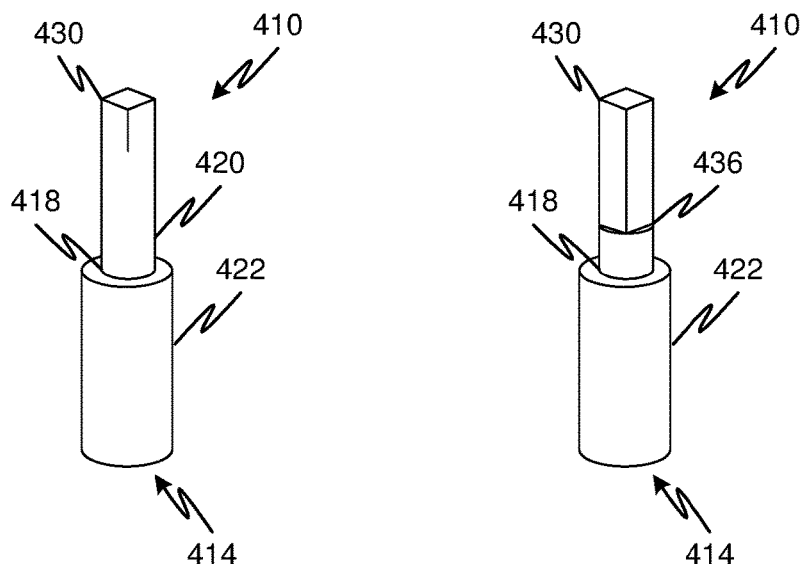
FIGS. 7A and 7B show respective embodiments of a blocking device in which only part of the blocking element is a solid of rotation according to embodiments of the disclosed subject matter.

Referring to FIG. 7A, an embodiment is shown that is not a solid of rotation in its entirety. In most ways a blocking element 410 is identical to the blocking element 110 of FIGS. 1A and 1B, for example, a second part 422 is a solid of rotation and has an opening 114 with a channel. A web 418 joins second part 422 to a first part 420. In the present embodiment the only difference is that a distal end 430 of the first part 420 is square and blends gradually into a round first part. Alternatively, the first part it could transition abruptly to a solid of rotation as indicated at 436 in FIG. 7B. That is, the first part gradually transitions from a square to a round where the web is formed. from a circular cross-section to a square cross-section. In other respects, the blocking element 410 is the same. Thus, the blocking element doesn't have to be a solid of rotation in its entirety.

Note that in embodiments, the web may be formed to be breakable or tearable by providing a selected non-uniform thickness or a series of perforations around it to ensure it is sufficiently weak that the blocking element reconfigures predictably.

Aspects describe methods of providing fluid to a fluid circuit, by attaching a fluid circuit to a fluid handling device where the fluid circuit includes a first portion with a container filled with fluid, and a second portion connected to the first portion by a tube blocked by a blocking element. In this aspect, the fluid handling device includes a controller used to reconfigure the blocking element and provide patency in the tube. The blocking element is reconfigured to apply a force by a forcing element (e.g., a motorized forcing element) against a wall of the tube to change a shape of the blocking element and hold the reconfigured shape of the blocking element using the forcing element while fluid is transferred from the container. In this aspect, the blocking element and tube are such that without holding the forcing element against the tube, the patency of the tube is diminished due to a tendency of the tube to return to its original shape before applying the force.

In another aspect, the blocking element is a solid of rotation, and the first and second portions are kept together while holding the reconfigured shape of the blocking element and maintaining a connection between the first and second portions. In another aspect, the controller is configured to open the tube in response to a first command or signal and to release the tube in response to a second command or signal. The second command or signal can be generated after fluid from the container has been consumed or is no longer needed. In addition, the fluid in the container can be used while the reconfigured shape is held.

In another aspect, the reconfiguring includes breaking the blocking element to open a hole therein.

In yet another aspect, the first portion is shaped and sized such that it can move freely in the tube but for an attachment between the first and second portions.

Many alternatives, modifications, and variations are enabled by the present disclosure. While specific embodiments have been shown and described in detail to illustrate the application of the principles of aspects described herein, it will be understood that aspects may be embodied otherwise without departing from such principles. Accordingly, Applicants intend to embrace all such alternatives, modifications, equivalents, and variations that are within the spirit and scope of the claims below.

What is claimed is:

1. A fluid channel sealing device, comprising:
    a fluid channel including a flexible tube with internal walls for conveyance of a fluid;
    a blocking element, at least a portion of which is sealingly engaged with the internal walls;
    the blocking element being reconfigurable from a first configuration free of any open channels such that fluid is prevented from flowing through the fluid channel; and a second configuration in which an open channel is established and allows fluid to pass wherein the second configuration is established by applying a deforming force on the blocking element to open a hole in the blocking element, a patency of the hole being maintained while the second configuration is maintained, wherein the blocking element has first and second parts that remain connected in said second configuration, and the blocking element is a solid of rotation with an axis of the blocking element aligned with an axis of the fluid channel, and the blocking element is reconfigurable by applying the deforming force crosswise to the axis of the blocking element, between the first and second parts.

2. The device of claim 1, wherein when the deforming force is applied to the blocking element between the first and second parts, the first and second parts partly separate to open the hole in the blocking element.

3. The device of claim 2, wherein when the first and second parts partly separate, the first and second parts remain at least partially connected.

4. The device of claim 1, wherein a diameter of the first part has a minimum dimension that is smaller than a diameter of the second part and smaller than a minimum internal size of the fluid channel such that the second part can hold a position in the fluid channel.

5. The device of claim 4, wherein the second part remains sealingly engaged with the internal walls after the first and second parts separate.

6. The device of claim 1, wherein the patency of the hole is maintained by continuously applying the deforming force to the blocking element.

7. The device of claim 1, wherein the patency of the hole is maintained by continuously applying the deforming force to the blocking element.

8. The device of claim 7, wherein the continuously applying the deforming force to the blocking element is at a location between the first and second parts.

9. The device of claim 1, wherein the blocking element is a frangible solid and the second configuration is established by fracturing the frangible solid between the first and second parts.

10. The device of claim 9, wherein the hole is maintained by preventing the blocking element in the second configuration from returning to the first configuration.

11. The device of claim 9, wherein a maximum size opening of the hole is maintained by preventing the blocking element from returning to an initial configuration in which a web connecting the first and second parts is intact.

12. The device of claim 9, further comprising a forcing driver aligned with the blocking element.

13. The device of claim 12, wherein the forcing driver is attached to a holder for the fluid channel, the holder aligning the fluid channel such that the blocking element is aligned with the forcing driver.

14. The device of claim 12, wherein the second configuration is established by the forcing driver generating the deforming force crosswise to an axis of the blocking element and fracturing the frangible solid between the first and second parts.

15. The device of claim 14, wherein the forcing driver maintains the blocking element in the second configuration after the fracturing to maintain the patency of the hole.

* * * * *